United States Patent [19]

Burckhalter

[11] Patent Number: 4,714,703
[45] Date of Patent: Dec. 22, 1987

[54] METHOD OF INHIBITING HERPETIC LESIONS

[76] Inventor: Joseph H. Burckhalter, 2201 Melrose, Ann Arbor, Mich. 48104

[21] Appl. No.: 846,841

[22] Filed: Mar. 31, 1986

Related U.S. Application Data

[63] Continuation of Ser. No. 774,902, Sep. 11, 1985, abandoned, which is a continuation of Ser. No. 672,148, Nov. 16, 1984, abandoned, which is a continuation of Ser. No. 485,997, Apr. 18, 1983, abandoned.

[51] Int. Cl.$^4$ .......................................... A61K 31/505
[52] U.S. Cl. ................................................. 514/274
[58] Field of Search ........................................ 514/274

[56] References Cited

U.S. PATENT DOCUMENTS 4,411,893 10/1983 Johnson et al. .................... 514/274

OTHER PUBLICATIONS

Chemical Abstracts 77:28676 p. (1972).
Bauer et al., Chemotherapy of Virus Diseases, vol. 1, Pergamon Press, N.Y., N.Y., 1973, p. 274.

*Primary Examiner*—Jerome D. Goldberg
*Attorney, Agent, or Firm*—Krass & Young

[57] ABSTRACT

A method is provided for inhibiting lesions associated with herpes simplex infection in warm blooded animals comprising administering to any such warm blooded animal a pharmaceutical composition in topical dosage form containing as active component the antimetabolite 5-fluorouracil.

5 Claims, No Drawings

METHOD OF INHIBITING HERPETIC LESIONS

CROSS-REFERENCE TO RELATED APPLICATION

This application is a continuation of application Ser. No. 774,902 filed Sept. 11, 1985, now abandoned, which is a continuation of Ser. No. 672,148 filed Nov. 16, 1984, now abandoned, which in turn is a continuation of Ser. No. 485,997 filed Apr. 18, 1983, now abandoned.

TECHNICAL FIELD

This invention is directed to pharmaceutical means in composition or dosage form containing an antiviral component that is a uracil compound and to methods for their use. The compositions are useful for inhibiting lesions associated with herpes simplex infection in warm blooded animals.

BACKGROUND OF THE INVENTION

A wide variety of methods have been used over the years for the symptomatic relief of pain and remission of lesions such as fever blisters or cold sores associated with infection caused by herpes simplex, type 1 or type 2. One way of treating the lesions presented by herpes simplex infection calls for topical application on the lesion of a pharmaceutical formulation that contains idoxuridine as the active ingredient. Idoxuridine is an antimetabolite that interferes with DNA synthesis. It is poorly water-soluble and is used as a dilute solution in a suitable non-aqueous vehicle or solvent such as dimethylsulfoxide. Another way of treating herpes simplex infection calls for topical application, on the lesion, of a formulation containing the antimetabolite vidarabine. However, attempts to modify genital or oral herpes simplex infection by local application of vidarabine have failed to show substantial benefit.

In view of the limitations of current therapy for treatment of lesions associated with herpes simplex infection, a need for additional therapeutic methods exists.

SUMMARY AND DETAILED DESCRIPTION

The present invention is based on the unexpected finding that 5-fluorouracil possess useful pharmacological properties for controlling and inhibiting lesions associated with herpes simplex infection. The invention in one aspect, therefore relates to pharmaceutical means in topical dosage form for the topical treatment and inhibition of herpetic lesions in warm blooded animals, embodying a lesion-inhibiting amount of 5-fluorouracil.

Pharmaceutical compositions contemplated by the invention can take any of a wide variety of topical dosage forms that may be prepared by conventional means. The compositions can be either solid or liquid. Solid form preparations include powders and suppositories. Suitable solid carriers are gelation, low melting wax, cocoa butter, and the like.

Liquid form preparations including solutions, suspensions, and emulsions. As an example may be mentioned water-propylene glycol solutions. Liquid preparations can also be formulated in solution in aqueous polyethylene glycol solution. Aqueous solutions can be prepared by dissolving the active component in water and adding suitable colorants, flavors, stabilizing, and thickening agents as desired. Aqueous suspensions suitable for topical use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, a solution or powder in vials or ampoules.

The quantity of active compound in a unit dose of preparation may be varied or adjusted according to the particular application.

In therapeutic use as a lesion-inhibiting agent, the compositions are constituted such that the active content of fluorouracil is at least about 0.1 percent by weight based on the total weight of the composition. Where the composition is a solution, the preferred content is in the range from about 2 to about 5 percent by weight. Where the composition is a cream or ointment, the preferred content is about 5 percent by weight. Compositions which are suitable for purposes of the invention are commercially available. For example, fluorouracil is available under the name Efudex R, Roche, as a 2 percent solution and a 5 percent solution compounded with propylene glycol, tris(hydroxymethyl)aminomethane, hydroxypropyl cellulose, parabens (methyl and propyl) and disodium edetate. It is also available as an ointment or cream, in a vanishing cream base consisting of white petrolatum, stearyl alcohol, propylene glycol, polysorbate 60 and parabens (methyl and propyl).

The invention in another aspect concerns a method of inhibiting lesions associated with herpes simplex infection, type 1 or type 2, in warm blooded animals comprising administering to any such warm blooded animal a lesion-inhibiting amount of a pharmaceutical composition in topical dosage form containing as active component at least about 0.1 percent by weight of 5-fluorouracil based on the total weight of the composition. In one preferred embodiment, the composition is a solution of 5-fluorouracil in propylene glycol, preferably containing from about 2 to about 5 percent by weight of 5-fluorouracil. In another preferred embodiment of the composition is a cream or ointment containing a minor proportion of 5-fluorouracil, preferably about 5 percent by weight. Administration is accomplished by applying the composition in suitable form such as a liquid, cream or ointment directly onto the surface of the lesion in an amount sufficient to cover the surface. Application is made once or twice daily. For the treatment of facial cold sores, two or three applications of the 5 percent cream or 5 percent solution in propylene glycol, if early enough in the course of infection, are ordinarily sufficient to prevent the normal course of the infection, characterized by increasing sensitivity followed by blisters or lesions, then a crust and scab with final sluffing of the scab. If applied early enough, no blister develops and hence no scab. If the composition is not applied at the first symptom but later, then typically the normal course of the infection follows, with much less severity than if not treated, fewer blisters, smaller blisters and a smaller scab.

Having thus described my invention, the embodiments in which an exclusive property or privilege is claimed are defined as follows.

I claim:

1. A method of inhibiting surface lesions associated with human herpes simplex infection comprising:
   administering to any such lesion an effective lesion-inhibiting amount of a pharmaceutical composition in topical dosage form containing as active component about 0.1 to about 5 percent by weight of 5-fluorouracil based on the total weight of the composition.

2. A method according to claim 1 where the composition is a solution of 5-fluorouracil.

3. A method according to claim 2 where the composition contains from about 2 to about 5 percent by weight of 5-fluorouracil.

4. A method according to claim 1 where the composition is a cream or ointment containing 5-fluorouracil.

5. A method according to claim 4 where the composition contains about 5 percent by weight of 5-fluorouracil.

* * * * *